(12) United States Patent
Biber (10) Patent No.: US 11,672,489 B2
(45) Date of Patent: Jun. 13, 2023

(54) METHOD AND SYSTEM FOR MONITORING A MOTION OF A SUBJECT, AND CORRESPONDING COMPUTER PROGRAM PRODUCT

(71) Applicant: Siemens Healthcare GmbH, Erlangen (DE)

(72) Inventor: Stephan Biber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 218 days.

(21) Appl. No.: 17/074,774

(22) Filed: Oct. 20, 2020

(65) Prior Publication Data
US 2021/0121131 A1 Apr. 29, 2021

(30) Foreign Application Priority Data
Oct. 28, 2019 (EP) .................................... 19205630

(51) Int. Cl.
| | |
|---|---|
| *A61B 5/00* | (2006.01) |
| *A61B 5/055* | (2006.01) |
| *G01R 33/34* | (2006.01) |
| *G01R 33/58* | (2006.01) |
| *G01S 11/02* | (2010.01) |
| *A61B 5/11* | (2006.01) |

(52) U.S. Cl.
CPC ............ *A61B 5/721* (2013.01); *A61B 5/0035* (2013.01); *A61B 5/055* (2013.01); *G01R 33/34* (2013.01); *G01R 33/583* (2013.01); *G01S 11/02* (2013.01); *A61B 5/1128* (2013.01)

(58) Field of Classification Search
CPC combination set(s) only.
See application file for complete search history.

(56) References Cited

U.S. PATENT DOCUMENTS

| | | |
|---|---|---|
| 2010/0106008 A1 | 4/2010 | Harvey |
| 2014/0070807 A1 | 3/2014 | Biber |
| 2015/0002331 A1 | 1/2015 | Allmendinger |
| 2016/0245888 A1 | 8/2016 | Bollenbeck |
| 2017/0074980 A1* | 3/2017 | Adib ....................... G01S 7/415 |

(Continued)

FOREIGN PATENT DOCUMENTS

| | | |
|---|---|---|
| DE | 102012216292 A1 | 5/2014 |
| EP | 3486672 A1 | 5/2019 |
| EP | 3796020 A1 | 3/2021 |

OTHER PUBLICATIONS

European Search Report for European Application No. 19205630.7-1010 dated May 11, 2020.

(Continued)

*Primary Examiner* — Joel F Brutus
(74) *Attorney, Agent, or Firm* — Lempia Summerfield Katz LLC (57) ABSTRACT

The disclosure relates to a method for monitoring a motion of a subject, as well as to a corresponding system and computer program product. As part of the method, a monitoring signal is emitted towards a corresponding receiver. The motion of the subject is then detected based on a change in the received monitoring signal. Therein, the monitoring signal is emitted using a spread-spectrum technique and/or using an M-to-N and multi-antenna emitter-receiver system with a set of M transmitting antennas and a set of N receiving antennas.

18 Claims, 2 Drawing Sheets

(56) References Cited

U.S. PATENT DOCUMENTS

2018/0143283 A1* 5/2018 Lips ................ G01R 33/56509
2021/0080526 A1 3/2021 Biber

OTHER PUBLICATIONS

Speier, P., M. Fenchel, and R. Rehner. "PT-Nav: a novel respiratory navigation method for continuous acquisitions based on modulation of a pilot tone in the MR-receiver." Proc European Society for Magnetic Resonance in Medicine and Biology 32 (2015): S97-S98.

* cited by examiner

FIG 1

METHOD AND SYSTEM FOR MONITORING A MOTION OF A SUBJECT, AND CORRESPONDING COMPUTER PROGRAM PRODUCT

The present patent document claims the benefit of European Patent Application No. 19205630.7, filed Oct. 28, 2019, which is hereby incorporated by reference.

TECHNICAL FIELD

The present disclosure relates to a method for monitoring a motion of a subject, such as a patient. The present disclosure further relates to a corresponding system and a corresponding computer program product.

BACKGROUND

With technological advances in medical techniques as well as in signal and data processing many applications may benefit from taking into account a motion of a respective subject, such as a patient. A known example for this is motion compensated imaging or image reconstruction, e.g., where a motion due to a heartbeat or a breathing motion of the patient may be taken into account to reduce image artefacts or blurring.

For example, in magnetic resonance imaging (MRI), it has been suggested to use a pilot tone method, wherein a test signal is transmitted outside of an MR frequency band, that is, a frequency band used for the magnetic resonance imaging. Such a test signal may have a spectral distance or frequency distance to the MR frequency band of about 0.1 MHz to 5 MHz or even up to, for example, 300 MHz with a frequency that may be a multiple of 2.5 MHz to keep intermodulation products or harmonic interference out of the MR frequency band.

Approaches that have been tried or suggested so far do, however, have some disadvantages. For example, it may require a lot of additional filtering effort on a receiver side or signal processing side to separate the frequency bands of the test signal and an MR signal, and even then it may be difficult to keep point artefacts or stripe artefacts caused by the test signal out of resulting MR images. At least in part this has to do with relatively high levels or signal strengths used for the test signal to achieve a sufficient signal-to-noise ratio. Here, another disadvantage or problem is that a transmission power for the test signal may be limited by a dynamic range of a receiver system of a respective MRI device. It is easily possible for the test signal to load the receiver system and in particular an analog compander in a range where additional noise or even nonlinearities in the receiver system or a receiver chain may be generated, which in turn may negatively affect image quality of resulting MR images. Furthermore, the test signal may lead to problems with electromagnetic compatibility (EMC) and/or electromagnetic emissions exceeding safety limits.

SUMMARY AND DESCRIPTION

It is an objective of the present disclosure to address these problems and to enable motion monitoring with improved robustness and reliability. The scope of the present disclosure is defined solely by the appended claims and is not affected to any degree by the statements within this summary. The present embodiments may obviate one or more of the drawbacks or limitations in the related art.

As disclosed herein, a method may be used for monitoring a motion of a subject, such as a patient. These may be motions caused by a heartbeat or breathing of the patient and/or other voluntary or involuntary movements. The presently described method may particularly successfully be employed for monitoring or detecting cyclical or repeating motions but is not necessarily limited thereto. In a process act of the method, a monitoring signal is emitted towards a corresponding receiver. The monitoring signal is an electromagnetic signal, such as a radio signal, that is transmitted wirelessly from a sender or transmitter, (e.g., a transmitting antenna), to the receiver.

The receiver may be placed on or at the subject or on a side of the subject opposite the transmitter. Correspondingly, on its way from the transmitter to the receiver, the monitoring signal may encounter the subject or interact with the subject, which, depending on the motion of the subject at that time, may influence the monitoring signal, e.g., lead to a detectable change in the monitoring signal.

Correspondingly, in another act of the method, the motion of the subject is detected based on a change in the received monitoring signal. For this, the received monitoring signal that is received or measured by the receiver may be recorded so that a change over time of the received monitoring signal may be detected by analyzing the recorded received monitoring signal. Additionally, or alternatively, the received monitoring signal may be compared to a provided reference signal or reference signal form. This reference signal may be or represent the unchanged, originally transmitted monitoring signal or, for example, a signal or signal form that is expected as the received monitoring signal for a predetermined state or motion of the subject.

In one variant of the method, the monitoring signal is emitted using a spread-spectrum technique. In an additional or alternative second variant of the method, the monitoring signal is emitted using an M-to-N multi-antenna emitter-receiver system with a set or number of N transmitting antenna and a set or number of N receiving antennas. In particular, the number M of transmitting antennas may be smaller than the number N of receiving antennas. It is, however, also possible for the numbers M and N to be equal.

The present disclosure is based on the insight or overarching idea that by adapting the transmission and reception of the monitoring signal an improved robustness and reliability for detecting and monitoring the motion may be achieved. To do so, both variants may be employed individually or in combination with each other. Using the spread-spectrum technique, (e.g., a spread-spectrum signal modulation), may be particularly advantageous to make the monitoring signal and therefore the monitoring or detection of the motion more robust or resistant against noise or interference, in particular from narrowband sources. It also advantageously enables use of lower peak levels of the monitoring signal compared to other approaches where an unmodulated test signal might be used. This makes it easier to comply with EMC safety limits and also means that more frequencies or frequency bands may be used for the monitoring signal, giving the presently described method improved flexibility and adaptability to respective local circumstances.

Because, as part of the spread-spectrum technique, an energy of the monitoring signal may be spectrally spread out, crosstalk or interference with other electronic equipment may also be limited. If, for example, the method is used in conjunction or connection with an imaging technique, such as magnetic resonance imaging (MRI), discrete image artefacts such as bright points, spots, or stripes in resulting images of the subject may more easily be avoided due to the monitoring signal being spectrally spread out, leading to an overall improved image quality. Using the spread-spectrum technique for emitting the monitoring signal may also bring with it or enable additional advantages and benefits that will be described further down below in connection with advantageous developments of the present disclosure.

The present disclosure is not limited to any one specific spread-spectrum technique so that any technique that spreads out the monitoring signal over a frequency band, in particular, a frequency band that is wider than the monitoring signal or its bandwidth before spreading it out or strictly needed for its transmission, may be used in the method.

Using the M-to-N multi-antenna emitter-receiver system, (e.g., an M-to-N transmission technique), may also make monitoring and detecting the motion of the subject more robust and reliable. For example, the multi-antenna emitter-receiver system may enable or provide multiple coupling paths for the monitoring signal through the subject and is therefore not reliant on a single such path. This may advantageously provide robustness or resistance against localized disturbances, interference, or signal blocking. It may also provide a spatial resolution for the motion when the N receiving antennas are arranged in a spatially spread out layout or pattern.

This may advantageously offer an additional aspect or additional data for verifying that a detected change in the monitoring signal does indeed represent or correspond to a motion of the subject. For example, a particular spatial pattern of the received monitoring signal or its change might be associated with the motion in question, whereas a different spatial pattern might be inconsistent with any physically possible motion and may therefore indicate a disturbance, interference, or measurement error. An example for the latter might be if a change in the monitoring signal, (e.g., above a predetermined threshold), is only detected in one of the receiving antennas. This would indicate a discontinuous motion of the subject that might not physically be possible, because neighboring parts of the subject might be connected to each other and therefore move in conjunction with each other and/or with smoothly changing amplitudes.

Regardless of which variant is used, it is a particular advantage that the present disclosure may be used to monitor the motion of the respective subject as part of an imaging technique or other observation or examination technique for the respective subject, or independent thereof, e.g., on its own. For example, the motion of the subject may be monitored during a preparation phase, where the subject might be positioned by medical personnel for later imaging or examination, e.g., in a situation with unpredictably moving personnel and devices as well as potential exposure of medical personnel to any emitted signals. In such situations the respective imaging technique may not be used reliably and safely.

In an advantageous development, a phase and an amplitude of the emitted monitoring signal is determined as a reference for detecting the change in the monitoring signal. In a first variant, this is done by making the emitted monitoring signal carry a predetermined digital signal and by performing a calibration of an analog emitter or transmitter that is used for emitting the monitoring signal. This calibration is performed prior to emitting or transmitting the monitoring signal. This means that the emitted monitoring signal is fully predetermined and therefore known in terms of its phase, amplitude and signal form or content and may thus reliably be used as a reference to detect any changes or deviations in the received monitoring signal.

In an additional or alternative variant, the reference is determined by coupling out a part of the monitoring signal to be emitted at the emitter or transmitter and providing this coupled out part directly to a signal processing unit configured for detecting the change in the monitoring signal. In particular, the coupled out part of the monitoring signal may be provided or transmitted to the signal processing unit via a wired, (and e.g., electromagnetically shielded), connection to the signal processing unit.

It may also be possible to place a reference receiver in close proximity to the emitter or transmitter used for emitting the monitoring signal. This means that at least the part of the emitted monitoring signal may be transmitted from the emitter to the reference receiver wirelessly but without passing through or being reflected from the subject and therefore without being influenced by the subject or its motion. The reference receiver may then be physically coupled to the signal processing unit for providing it with the monitoring signal received as a reference by the reference receiver through a wired connection or transmission path.

In these additional or alternative variants, the actually sent or emitted monitoring signal may advantageously directly be used as the reference as it is actually sent, even without any predetermination or prior knowledge of its properties before transmission. Here, determining the phase and amplitude of the emitted monitoring signal may mean that these properties are measured for the coupled out part of the monitoring signal by the signal processing unit.

The reference or reference signal determined here may advantageously enable a particularly precise, robust, reliable, and fast detection of any changes in the monitoring signal and therefore of the motion of the subject.

In a further advantageous development in the variant where the monitoring signal is emitted using the spread-spectrum technique, the spread out monitoring signal is generated through a modulation with a predetermined pseudo-random spreading code. In other words, the monitoring signal or a digital signal carried thereby is combined with the pseudo-random spreading code to spread out the monitoring signal or its information content or energy. Using a pseudo-random spreading code may advantageously make the spectrally spread-out emitted monitoring signal particularly similar to broadband noise. This in turn means that any effects or artefacts caused by the monitoring signal in any other equipment or parallel data or signal processing, such as imaging data of the subject obtained while monitoring the motion by the monitoring signal, may appear as random noise. This advantageously may improve an image quality and/or limit or avoid false positive detections of features due to artefacts caused by the monitoring signal.

In a further advantageous development, the motion monitoring is combined with a magnetic resonance-based method for imaging the subject, e.g., with MRI. Therein, a frequency or a frequency band of the monitoring signal is set to partly or fully overlap a frequency band of a magnetic resonance imaging signal used for imaging the subject. The monitoring signal for monitoring the motion of the subject and a useful signal for the MRI do, in other words, spectrally overlap. The monitoring signal and the useful signal for the MRI, e.g., the magnetic resonance imaging signal, may also temporarily overlap each other, meaning that they may be transmitted and/or received simultaneously or during the same predetermined windows or period of time, for example, during application of a predetermined MRI sequence or a respective MR acquisition window. The magnetic resonance imaging signal in this sense may include RF-pulses emitted as part of the MRI process and/or a corresponding magnetic resonance echo signal received as part of the MRI process.

Using at least partially the same frequency or frequency band for the monitoring signal and the MRI signal or MR imaging process has the advantage of reducing or avoiding hardware complexity such as additional filters for separating different frequencies or frequency bands. Also, at least part of the hardware used for the magnetic resonance imaging, (in particular, one or more coils of a corresponding MRI device), may then also be used for transmitting or receiving the monitoring signal without any significant modifications, further reducing hardware complexity and cost. A further advantage is that this proposed development enables calibration or testing of at least part of a signal chain used for the magnetic resonance imaging through or by the monitoring signal, which may be generated more easily and safely than the actual magnetic resonance imaging signal.

Separation of the monitoring signal and the MRI signal may advantageously be done in software, which may reduce cost and complexity and provide increased flexibility and adaptability of the proposed method compared to a fully hardware-dependent solution. Particularly when using the spread-spectrum technique the spectral (and possibly temporal) overlap of the monitoring signal and the magnetic resonance imaging signal does in practice not lead to any coherent image interference or artefacts. This is the case, because the monitoring signal may be made so weak or low level that it may disappear in a noise level of the MRI signal. This advantageously offers the possibility to forego active suppression of the monitoring signal in the received MRI signal before generating or reconstructing a respective magnetic resonance image therefrom.

In a further advantageous development, a coil used for a magnetic resonance imaging is also used for emitting and/or receiving the monitoring signal. As described, this may advantageously reduce the amount of required hardware and therefore corresponding complexity and cost and may allow for easy and effective calibration and/or testing of at least part of the MRI signal chain by using the monitoring signal. The monitoring signal may be received by at least one MRI local coil, e.g., by an array of multiple spatially distributed MRI local coils. Local coils in this sense are coils that are intended or configured for placement on or at the subject for the MRI process.

However, for emitting the monitoring signal, at least one separate transmitting antenna that is different from an MRI transmitting coil is used. The separate transmitting coil used for emitting more transmitting the monitoring signal is, in other words, not used in the magnetic resonance imaging of the subject. The at least one separate transmitting antenna may be integrated in or with the MRI transmitting coil or at least a housing of a respective MRI device or system.

This approach, (e.g., using dedicated antennas or hardware for emitting the monitoring signal and not using antennas, coils, or hardware used or configured for the magnetic resonance imaging), may advantageously provide more flexibility, precision, and reliability both for monitoring the motion and for imaging the subject. This may be the case at least in part because RF-pulses emitted using the MRI transmitting coil for the magnetic resonance imaging and the monitoring signal may differ from each other significantly in terms of power, timescale or signal length, dynamic range, signal form, et cetera. Therefore, using different hardware for transmitting the monitoring signal and transmitting the RF-pulses for the magnetic resonance imaging may offer significant optimization potential.

For example, a transmitting power for the RF-pulses for the magnetic resonance imaging may be on the order of several kilowatts, while the transmitting power for the monitoring signal may be on the order of several microwatts or even nanowatts. Similarly, a timescale or length of the RF pulses may be on the order of at most a few milliseconds while the monitoring signal may be emitted over periods of, for example, more than 100 ms at a time.

Using dedicated transmitting antennas for emitting the monitoring signal may also represent a relatively easy and cheap to implement way for realizing the multi-antenna emitter-receiver system for the M-to-N transmission technique for the monitoring signal, because the transmitting antennas for the monitoring signal may be significantly smaller and cheaper than the MRI transmitting coil or coils and might, for example, not require a similarly sophisticated cooling system as the MRI transmitting coil or coils.

In a further advantageous development, the monitoring signal, in particular its energy, is uniformly spread out over a predetermined frequency band using the spread-spectrum technique. A signal level or signal strength of the monitoring signal is set so that at each frequency it is at or below a noise level of a received, (e.g., measured or detected), magnetic resonance echo signal, e.g., of the MR echo signal or signals from which an MR image of the subject is to be generated or reconstructed as part of the magnetic resonance based imaging of the subject. The received monitoring signal is then separated from the received MR echo signal through signal averaging over at least one time period that is long relative to or compared to a measurement period, such as an or acquisition window, defined in a respective MR imaging sequence or protocol, e.g., over at least 100 milliseconds (ms).

The measurement period in this sense is a period or window of time during which the MR echo signal, (e.g., an echo train), is received or recorded. With the level of the monitoring signal set relatively low in this manner even imperfect separation or suppression of the monitoring signal in the MR echo signal does advantageously not lead to a significantly reduced image quality or spatially discrete image artefacts, because the energy of the monitoring signal is uniformly spread out. This limits any influences of the monitoring signal on the reconstructed MR image to similarly spread out noise. As mentioned, this means that a complexity or sophistication of a signal processing for reconstructing the MR image may advantageously be reduced effectively without any significant negative effects. Even so, the motion of the subject may still be monitored, because measurement or detection of the monitoring signal is not limited by the timescale or sequence of the magnetic resonance imaging process or signal, which allows for separating out or extracting the monitoring signal over the mentioned relatively long period or periods of time.

The monitoring signal might on shorter timescales appear as noise, but because it is actually not true noise but rather a predetermined signal, it may be separated from any true noise by averaging which only averages out the random noise but not the actually not-random monitoring signal which therefore becomes more pronounced. While timescales of, for example, 100 ms are long relative to or compared to signaling timescales of individual RF-pulses and echoes of the magnetic resonance imaging process or sequence, they are still relatively short compared to a speed or timescale of macroscopic motions or movements of a subject or patient. Therefore, even with the described averaging the motion of the subject may still be reliably and, at least for practical purposes, continuously tracked or monitored.

In a further advantageous development, the received monitoring signal and the MR echo signal are measured together, for example as a combined signal. For separating out the received monitoring signal from the measured combined signal a (e.g., complex) weighting factor for minimizing a correlation between the two signal parts, (e.g., the monitoring signal and the MR echo signal), is determined and applied to the combined measured signal. By determining and applying the weighting factor in this manner, it becomes possible to subtract the monitoring signal and thus allow for monitoring the motion as well as for reconstructing an artefact-free MR image even though the monitoring signal and the MR echo signal may spectrally overlap each other. This signal processing to separate the monitoring signal from the MR echo signal may advantageously be performed in software, e.g., without necessarily relying on dedicated or specialized hardware, and may thus provide improved flexibility and adaptability and a relatively cheap and easy avenue for optimization.

Optimally, a weighting factor would be determined that leads to a correlation of zero between the two signal parts. But even if that cannot be readily achieved, resulting in an imperfect separation of the two signal parts, potential negative effects may be mitigated through the spread-spectrum technique as described.

In a further advantageous development, a signal reception chain through which the MR echo signal is received and processed is continuously or regularly calibrated or recalibrated during the magnetic resonance imaging and the parallel motion monitoring based on detected variations in the received monitoring signal that are not associated with, e.g., do not correspond to the motion of the subject. Such variations may include a drift of the received monitoring signal in one direction over time. They may also be variations on a different timescale than a motion or movement of the subject, and/or the like. These variations or fluctuations, (e.g., in a signal gain), may be continuously recorded. The variations or fluctuations may then be used as a basis for calibrating or recalibrating the signal reception chain. They may also be used as a basis for quality testing of the signal reception chain or as a reference for improving signal stability, for example, in applications with particularly high demands for signal stability.

Such variations in the received monitoring signal that are not associated with the motion of the subject may be caused by changes in temperature of the signal reception chain during operation, by increasing or decreasing surrounding humidity, by interference or disturbances in an electric supply or grid, by external sources of interference, and/or the like. Here, the monitoring signal may not only be used for monitoring a motion of the subject, but also for improving an accuracy and reliability of any measured signals and/or corresponding signal processing or any results based thereon. This may advantageously be achieved without additional hardware.

In a further advantageous development, a length of a predetermined pseudo-random spreading code used to spread out the monitoring signal as part of the spread-spectrum technique is set so that the monitoring signal is spread out across the full bandwidth of an MRI receiving coil or coils or a full width of a frequency band used for the magnetic resonance imaging. By using such a long spreading code, the method for monitoring the motion of the subject may be made particularly robust against external interference or disturbances. Also, by maximally spreading out the monitoring signal within the limits or boundaries of the hardware used for the magnetic resonance imaging the level or signal strength of the monitoring signal may be minimized without compromising its function, thereby reducing or minimizing any effects of the monitoring signal on the image quality of the respective MR images. In particular, these advantages may be achieved without requiring any additional or modified hardware, which advantageously reduces corresponding complexity and cost.

In a further advantageous development, the motion monitoring using the M-to-N multi-antenna emitter-receiver system is combined with a magnetic resonance-based method for imaging the subject. Therein, a frequency or frequency band of the monitoring signal is set to be outside of the frequency or frequency band used for the magnetic resonance imaging. Using different frequencies or frequency bands for the motion monitoring on the one hand side and for the MR-based imaging of the subject on the other hand side may advantageously limit interference or interplay between respective signals and may provide a straightforward way of separating the respective signals for both purposes. It may potentially also enable reception or measurement of the monitoring signal even during transmission of the RF-pulses for the magnetic resonance imaging. This may not be possible when the same frequencies are used, because the RF-pulses would overpower and drown out the monitoring signal due to their, e.g., several orders of magnitude higher power output. Therefore, using different frequencies or frequency bands advantageously enable continuous monitoring of the motion of the subject.

Additionally, using different frequencies enables improved flexibility and adaptability of the presently proposed method to local circumstances, because the frequency or frequency band used for the motion monitoring does not have to be tied to the fixed and unchangeable frequency or frequency band for the magnetic resonance imaging. This may enable the use of the proposed method for motion monitoring even when, for example, in a particular situation a narrowband source of interference or noise is present, because then a different frequency or frequency band may be used for the monitoring signal.

The frequency or frequency band for the monitoring signal may be manually or automatically be selected in dependence of an ambient spectrum of interference or noise that is respectively present, for example, at the location of the subject in any given situation or at any given application of the presently proposed method. For this purpose, the ambient electromagnetic spectrum or noise may be measured and analyzed, (e.g., automatically), to determine a suitable frequency or frequency band for the monitoring signal. For example, a frequency or frequency band with a local minimum of noise, activity or transmitted energy that is closest to the frequency band used for the magnetic resonance imaging may automatically be used or selected for the monitoring signal. This may be advantageous, because if a spectral distance or frequency distance between the frequency or frequency bands for the monitoring signal and the magnetic resonance imaging is lower or smaller than a predetermined threshold, it may be possible to use at least part of a signal chain for the magnetic resonance imaging also for the transmission or reception and/or processing of the monitoring signal.

In a further advantageous development, the monitoring signal is emitted and/or received at least between pulses, e.g., the mentioned RF-pulses, of the respective magnetic resonance imaging sequence that is applied for imaging the subject. The monitoring signal is, in other words, emitted and/or received for example after one or more, (e.g., after each), RF-pulse of the MRI sequence during an echo time or during measurement of the MR echo signal. Alternatively, or additionally, the monitoring signal may be emitted and/or received after measurement of a respective MR echo signal and before the respective next RF-pulse of the MRI sequence e.g., during the MRI sequence but not actually at the time of transmission of the MR pulses. This means that the monitoring signal may be emitted and/or received during at least part of a respective MR acquisition window.

This means that the motion of the subject may actually be monitored during the acquisition of MR data from which the respective MR image of the subject may be reconstructed. Therefore, a particularly precise temporal correlation between measured MR data, (e.g., the received MR echo signal), and the determined motion of the subject may be achieved. In particular, no extrapolation or interpolation might be necessary for determining the actual motion of the subject during the MR acquisition window.

It is, however, also possible to emit and/or receive the monitoring signal outside of the respective MR acquisition window. This might be useful for the mentioned averaging and/or for continuously monitoring the motion of the subject, (for example, between or across multiple MR data acquisitions, observations, and/or examinations of the subject), to enable continuity of corresponding motion data and therefore of knowledge of a respective position of the subject.

In a further advantageous development, the monitoring signal is emitted using the spread-spectrum technique and using multiple emitters of the M-to-N multi-antenna emitter-receiver system at the same time. Therein, different modulations that are orthogonal with respect to each other are used for emitting the monitoring signal through the multiple emitters. In other words, multiple parts or instances of the monitoring signal are emitted from different ones of the multiple emitters at the same time with each part or instance using a different modulation.

These different modulations may be based on or generated using orthogonal spreading codes. Separation of the multiple parts or instances of the monitoring signal, which may also be interpreted as multiple parallel monitoring signals, is then possible due to the orthogonality of their modulations or the respective spreading codes. This means, that effectively a code multiplexing method may be applied to the motion monitoring. In particular, separation of the multiple parallel monitoring signals is even possible when the same frequency or a frequency band is used for some or all of the multiple parallel monitoring signals, e.g., when they spectrally overlap.

It is, however, also possible to use separate or only partly overlapping frequencies are frequency bands for some or all of the multiple parallel monitoring signals. A separation of these frequencies are frequency bands may then be achieved or supported for example by respective frequency filters.

Using multiple emitters and thus multiple coupling paths of or for the monitoring signal through the subject and emitting the multiple parallel monitoring signals at the same time may advantageously provide additional information and thus a more robust, reliable, and complete determination or characterization of the motion of the subject.

Because the emitters or transmission antennas may be relatively small, achieving this does advantageously not require an unreasonable amount of effort or cost.

Another aspect of the present disclosure is a system for monitoring a motion of a subject. The system includes an emitting device (or emitter) for emitting or transmitting a predetermined monitoring signal, a receiving device (or receiver) for receiving the emitted or transmitted monitoring signal, and a signal processing unit (or processor) for detecting the motion of the subject based on a change in the received monitoring signal. The system is configured to, automatically or semi-automatically, execute or perform the method disclosed herein. Because, as described in connection with the method, a combination with an imaging process for imaging the subject is possible, (e.g., with a magnetic resonance based imaging process), the system may also include a corresponding imaging device, such as an MRI device or MRI subsystem.

Because the system is configured to carry out the method, the system may include any or all of the advantages, developments, and/or components or devices mentioned in connection with the method, and/or may be configured to carry out any additional acts, procedures, or processes mentioned in connection with the method.

The emitting device may include at least one transmission antenna, in particular the set of M transmitting antennas of the multi-antenna emitter-receiver system. The emitting device may also include a signal generator for generating the monitoring signal, and/or other signal processing or signal forming components.

The receiver may include at least one receiver or receiving antenna, in particular the set of N receiving antennas of the multi-antenna emitter-receiver system. The receiver may also include additional components or parts, such as a filter, etc. The receiver may be coupled or connected to the signal processing unit through a wired connection over which the monitoring signal received by the receiver may be (directly) provided to the signal processing unit.

The signal processing unit may include one or more electric and/or electronic circuits, a processor such as a microchip or microprocessor, a data store connected thereto with an operating system or program code stored thereon, and/or the like. This data store and/or program code may represent or encode the process acts of the method and they may themselves be another aspect in the form of a computer program product. The computer program product includes instructions to cause the system to, automatically or semi-automatically, execute the method. The computer program product may be a computer program or program code executable by a processing device, e.g., the system or its signal processing unit. The method may be partly or fully computer implemented. The computer program product may also be a computer-readable storage medium, whereon such a computer program or program code is stored.

The embodiments and developments described herein for at least one aspect of the present disclosure, that is, at least for the method, the system, and the computer program product, as well as the corresponding advantages may be applied to any and all aspects of the present disclosure.

BRIEF DESCRIPTION OF THE DRAWINGS

Further advantages, features, and details of the present disclosure derive from the following description of embodiments as well as from the drawings. The features and feature combinations previously mentioned in the description as well as the features and feature combinations mentioned in the following description of the figures and/or shown in the figures alone may be employed not only in the respectively indicated combination but also in other combinations or taken alone without leaving the scope of the present disclosure. In the drawings.

The examples described below refer to embodiments of the present disclosure. Therein, individual components and process acts of the embodiments each constitute individual, independent features of the present disclosure that may further develop the disclosure independently of each other as well as in combinations not explicitly described. The described embodiments may be further developed or supplemented by features, components, and/or acts already described above.

DETAILED DESCRIPTION

Figure 1:
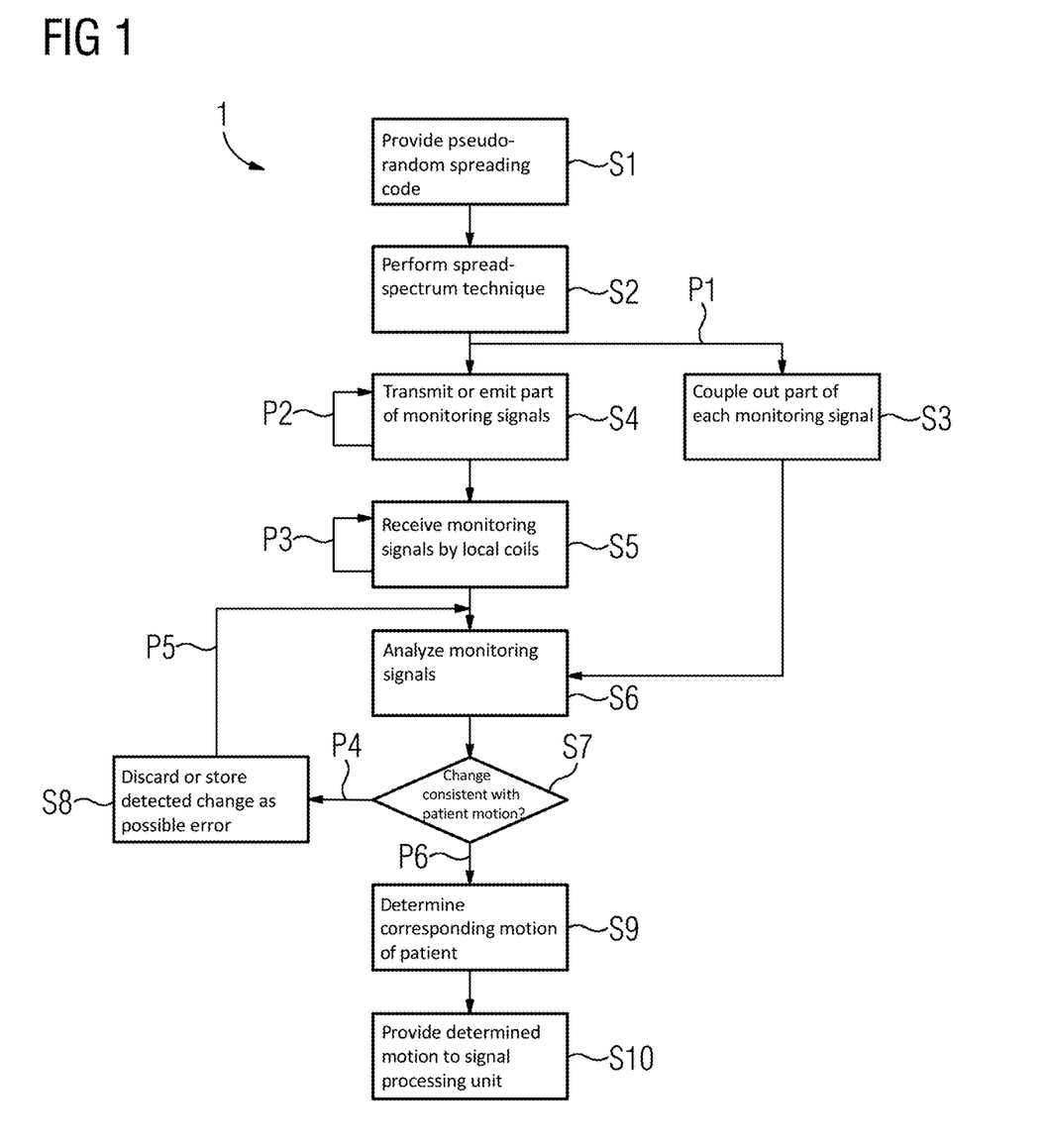
FIG. 1 schematically illustrates an example of a flow chart for a method for monitoring a motion of a subject.
Figure 2:
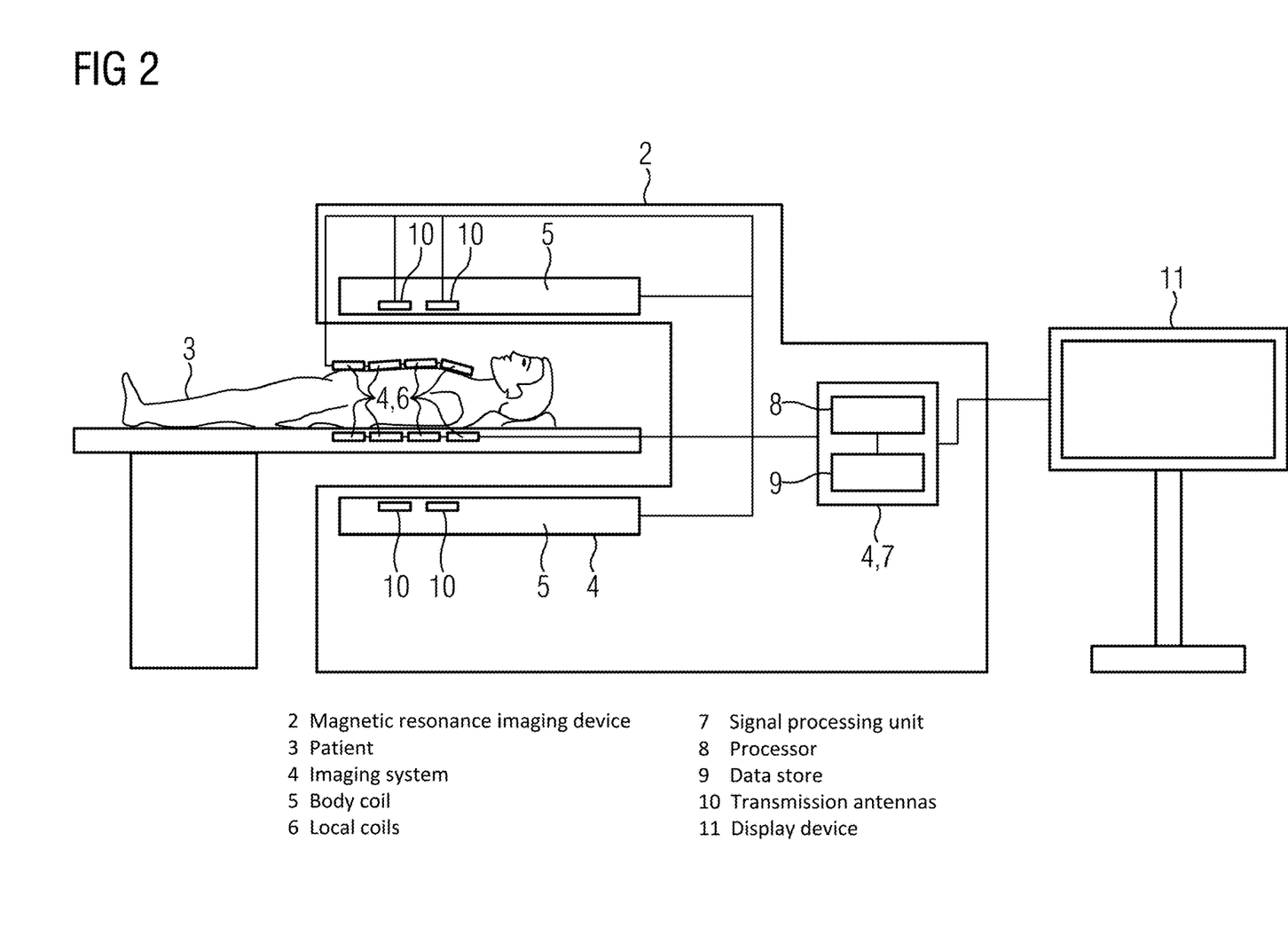
FIG. 2 schematically illustrates an example of a system for carrying out the method.

FIG. 1 schematically depicts an example for a flow chart 1 for a method for monitoring a motion of a subject. This method is illustrated here by process acts S1 to S10 and program paths P1 to P6, both of which may represent corresponding instructions, routines, or program modules of a corresponding computer program or computer program product. This computer program and therefore the corresponding method may be carried out by a system which is schematically illustrated in FIG. 2 as an MRI device 2. Below, the method, (the flow chart 1), will be explained with reference to FIG. 1 and FIG. 2.

The MRI device 2 is presently configured to image a patient 3 based on a magnetic resonance imaging technique. Here, the patient 3 serves as the subject whose motion is to be monitored using the mentioned method. In particular, the motion of the patient 3 shall be monitored while magnetic resonance imaging data (MR data) of the patient 3 is acquired by the MRI device 2. The MRI device 2 presently includes an imaging system 4, which is also only schematically represented here. The imaging system 4 includes at least a body coil 5 surrounding the patient 3 and configured to generate a magnetic field in a volume occupied by the patient 3. The imaging system 4 also includes multiple local coils 6 which are presently arranged in close proximity to the patient 3, in particular on and under him. Furthermore, the imaging system 4 also includes a signal processing unit 7, which is connected to some or all of the coils 5, 6.

The signal processing unit 7 presently includes a processor 8 and connected thereto a data store 9, and is configured to process MR echo signals, e.g., MR data received or measured by the local coils 6. The signal processing unit 7 may also be configured to control the body coil 5 or a sequence of RF-pulses transmitted therewith as part of the magnetic resonance imaging process. Respective MR images of the patient 3 generated or reconstructed from the MR data by the signal processing unit 7 may be displayed using a connected display device 11.

While the signal processing unit 7 is represented as a single unit this is to be understood as purely exemplary and schematically. In a practical implementation, the signal processing unit 7 may be divided into or include several individual units for the multiple functions or purposes of the signal processing unit 7 as described herein.

The data store 9 may contain a computer program that may be executed by the processor 8 and that includes instructions representing the method for monitoring the motion of the patient 3, (e.g., the flow chart 1), to cause the processor 8 or the signal processing unit 7 or the MRI device 2 to execute the method.

In process act S1, at least one pseudo-random spreading code is provided. Multiple orthogonal spreading codes may be provided. The spreading codes may be stored in or loaded into the data store 9.

In process act S2, a spread-spectrum technique is performed to generate a spectrally spread out monitoring signal based on the provided pseudo-random spreading code. If multiple spreading codes are provided, multiple different corresponding modulations may be performed to generate multiple different monitoring signals or multiple differently modulated instances of the monitoring signal. This may be automatically performed by the signal processing unit 7.

As indicated by a program path P1, a part of each monitoring signal is coupled out in process act S3 as a reference representing the original or unchanged monitoring signal as intended for transmission. Respective remaining parts of the monitoring signals are transmitted or emitted in process act S4 by dedicated transmission antennas 10. These transmission antennas 10 are presently integrated into or arranged in the body coil 5 but are actually individually controllable devices. Each of the transmission antennas 10 is used to emit a differently modulated one of the monitoring signals with orthogonal modulations towards the patient 3 and the local coils 6. The monitoring signals may be continuously or regularly emitted, which is indicated here by a looping program path P2.

In process act S5, the parts of the monitoring signal is transmitted by the transmission antennas 10 are received by the local coils 6. At the same time, the patient 3 might be moving, (e.g., due to a breathing motion), which influences the received monitoring signal. Corresponding to the continuous or regular transmission of the monitoring signal, the signals may also be received continuously or regularly as indicated by a looping program path P3.

The monitoring signals received by the local coils 6 are provided to the signal processing unit 7 via a wired connection. In process act S6, the signal processing unit 7 analyzes the received monitoring signals to determine a change corresponding to or indicating the motion of the patient 3.

For this purpose, the monitoring signals received by the local coils 6 may be compared to the part of the original monitoring signal that was coupled out in process act S3. This coupled out part may be kept in the signal processing unit 7 or may be coupled out and the transmission antennas 10 and directly provided to the signal processing unit 7 through a wired connection without being subjected to any potentially signal changing influence of the patient 3 or his motion.

In process act S7, it is determined if a detected change in the monitoring signal is consistent with possible motions of the patient 3. These possible motions and/or corresponding changes in the monitoring signals, (e.g., in terms of an amount of change, a speed of change, and/or a spatial distribution or a pattern of change), may be experimentally (pre-)determined and provided as input data for the signal processing unit 7. If it is determined that the detected change is inconsistent with a motion of the patient 3 or inconsistent with being caused by the motion of the patient 3, the flow chart 1 follows program path P4 to process act S8.

In process act S8, the detected change might be discarded or stored as an indication of a possible error for later analysis. As indicated by program path P5, the method may then continue to detect any additional subsequent changes in the monitoring signals, because they may be continuously or regularly received or recorded. If at one point or in one iteration of process act S7 it is determined that a detected change in the monitoring signal is consistent with a motion of the patient 3 or with being caused by the motion of the patient 3, the flow chart 1 follows program path P7 to process act S9.

In process act S9, the corresponding motion of the patient 3 is determined by the signal processing unit 7.

In process act S10, the determined motion or corresponding motion data characterizing or describing this motion may be provided by the signal processing unit 7 or one of its functions or modules as an output, (e.g., to another function, module, subroutine, or device). For example, the motion data may be provided to an image reconstruction module of the signal processing unit 7 that is configured to reconstruct a motion-compensated MR image of the patient 3 based on the received MR data and the determined motion of the patient 3.

While the method for monitoring or detecting the motion of the patient 3 has he been described in connection with magnetic resonance imaging of the patient 3, the method may also be performed independently thereof. It is also to be understood that the signal processing unit 7 may (depending on an implementation of the described method) be configured to separate different frequency bands used for the monitoring signals and/or the RF-pulses or MR echo signals, and/or be configured to separate corresponding different signal portions when overlapping frequencies or frequency bands are used. In particular, the concept of co-transmitting the monitoring signal in the frequency band used for the magnetic resonance imaging and using subtraction coefficients (wk or time-dependent: wk(t)) determined for separating signals and thereby cleaning or correcting the MR data or corresponding MR image as useful information, (e.g., for determining the motion of the patient 3), may analogously be used in or applied to other applications. Also, the broadband spreading out of the monitoring signal may enable additional ways of handling, using, or processing the monitoring signal for different types of applications and situations.

In summary, the described examples show how a patient motion or movement may be monitored by a spread-spectrum modulated test signal and corresponding transmission and receiving antennas or arrays.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the disclosed embodiments, the disclosure is not limited to the disclosed examples. Other variations may be deducted by those skilled in the art without leaving the scope of protection of the claimed disclosure.

The invention claimed is:

1. A method for monitoring a motion of a subject, the method comprising:
   generating a monitoring signal;
   coupling out a part of the monitoring signal to provide a reference monitoring signal as intended for transmission;
   emitting, by an emitter, a respective remaining part of the monitoring signal towards a corresponding receiver;
   receiving, by the corresponding receiver, the emitted monitoring signal to provide a received monitoring signal;
   comparing, by a signal processing unit, the reference monitoring signal and the received monitoring signal; and
   detecting, by the signal processing unit, the motion of the subject based on a change between the reference monitoring signal and the received monitoring signal,
   wherein the respective remaining part of the monitoring signal is emitted toward the corresponding receiver: using a spread-spectrum technique, using an M-to-N multi-antenna emitter-receiver system with a set of M transmitting antennas and a set of N receiving antennas, or a combination thereof.

2. The method of claim 1, wherein a phase and an amplitude of the emitted monitoring signal are determined as a reference for the detecting of the motion of the subject.

3. The method of claim 1, wherein, when the monitoring signal is emitted using the spread-spectrum technique, the monitoring signal is generated through modulation with a predetermined pseudo-random spreading code.

4. The method of claim 1, wherein the motion monitoring is combined with a magnetic resonance imaging of the subject, and
   wherein a frequency of the monitoring signal is set to overlap a frequency band of a magnetic resonance imaging signal.

5. The method of claim 4, wherein a coil used for the magnetic resonance imaging of the subject is also used for the emitting of the monitoring signal, the receiving of the monitoring signal, or a combination thereof.

6. The method of claim 5, wherein the monitoring signal is emitted by at least one transmitting antenna,
   wherein the monitoring signal is received by at least one magnetic resonance local coil,
   wherein the at least one transmitting antenna is separate from at least one magnetic transmitting coil.

7. The method of claim 6, wherein the magnetic resonance local coil comprises an array of multiple spatially distributed magnetic resonance local coils.

8. The method of claim 4, wherein the monitoring signal is uniformly spread out over a predetermined frequency band using the spread-spectrum technique,
   wherein a signal level of the monitoring signal is set so that, at each frequency, the signal level is at or below a noise level of a received magnetic resonance echo signal, and
   wherein the received monitoring signal is separated from the received magnetic resonance echo signal through signal averaging over at least one time period that is longer compared to a measurement period defined in a respective MR imaging sequence.

9. The method of claim 8, wherein the at least one time period is at least 100 milliseconds.

10. The method of claim 4, wherein the received monitoring signal and a magnetic resonance echo signal are measured together and, for separating out the received monitoring signal, a weighting factor for minimizing a correlation between two signal parts is determined and applied to the measured signal.

11. The method of claim 4, wherein a signal reception chain through which a magnetic resonance echo signal is received and processed is continuously or regularly calibrated during the magnetic resonance imaging and the motion monitoring based on detected variations in the received monitoring signal that are not associated with the motion of the subject.

12. The method of claim 4, wherein a length of a predetermined pseudo-random spreading code used to spread out the monitoring signal as part of the spread-spectrum technique is set so that the monitoring signal is spread out across a full bandwidth of a magnetic resonance imaging receiving coil or coils or a full width of the frequency band used for the magnetic resonance imaging.

13. The method of claim 4, wherein the monitoring signal is emitted and received at least between pulses of a magnetic resonance imaging sequence that is applied for imaging the subject.

14. The method of claim 1, wherein the motion monitoring using the M-to-N multi-antenna emitter-receiver system is combined with a magnetic resonance imaging of the subject, and wherein a frequency of the monitoring signal is set to be outside of a frequency band used for the magnetic resonance imaging.

15. The method of claim 1, wherein the monitoring signal is emitted using the spread-spectrum technique and using multiple emitters of the M-to-N multi-antenna emitter-receiver system at a same time, and wherein different modulations that are orthogonal with respect to each are used for emitting the monitoring signal through the multiple emitters.

16. The method of claim 15, wherein the different modulations that are orthogonal with respect to each other are based on orthogonal spreading codes.

17. A system configured to monitor a motion of a subject, the system comprising:

an emitter configured to emit a part of a monitoring signal to provide an emitted monitoring signal, wherein a remaining part of the monitoring signal is configured to be coupled out to provide a reference monitoring signal as intended for transmission;

a receiver configured to receive the emitted monitoring signal to provide a received monitored signal; and a signal processor configured to compare the reference monitoring signal and the received monitoring signal detect the motion of the subject based on a change between the reference monitoring signal and the received monitoring signal, wherein the part of the monitoring signal is configured to be emitted towards the corresponding receiver: (a) using a spread-spectrum technique, (b) using an M-to-N multi-antenna emitter-receiver system with a set of M transmitting antennas and a set of N receiving antennas, or a combination thereof.

18. A non-transitory computer program product comprising instructions, wherein the instructions, when executed by a processor, cause a system to:

emit a part of a monitoring signal towards a corresponding receiver to provide an emitted monitoring signal, wherein a remaining part of the monitoring signal is coupled out to provide a reference monitoring signal as intended for transmission;

receive, by the corresponding receiver, the emitted monitoring signal to provide a received monitoring signal;

compare, by a signal processing unit, the reference monitoring signal and the received monitoring signal; and detect, by the signal processing unit, a motion of a subject based on a change between the reference monitoring signal and the received monitoring signal, wherein the part of the monitoring signal is emitted towards the corresponding receiver: using a spread-spectrum technique, using an M-to-N multi-antenna emitter-receiver system with a set of M transmitting antennas and a set of N receiving antennas, or a combination thereof.

* * * * *